United States Patent [19]

Trick

[11] Patent Number: 4,790,298

[45] Date of Patent: Dec. 13, 1988

[54] PENILE PROSTHESIS AND METHOD

[75] Inventor: Robert E. Trick, Racine, Wis.

[73] Assignee: Medical Engineering Corporation, Racine, Wis.

[21] Appl. No.: 82,155

[22] Filed: Aug. 5, 1987

[51] Int. Cl.⁴ .............................. A61F 2/26
[52] U.S. Cl. ..................................... 128/79
[58] Field of Search ......................... 128/79

[56] References Cited

U.S. PATENT DOCUMENTS

| | | | |
|---|---|---|---|
| 4,151,840 | 5/1979 | Barrington | 128/79 |
| 4,522,198 | 6/1985 | Timm et al. | 128/79 |
| 4,545,081 | 10/1985 | Nestor et al. | 128/79 |
| 4,619,251 | 10/1986 | Helms et al. | 128/79 |
| 4,666,428 | 5/1987 | Mattioli | 128/79 |

Primary Examiner—Gene Mancene
Assistant Examiner—Cary E. Stone
Attorney, Agent, or Firm—S. E. Krieger

[57] ABSTRACT

The penile prosthesis includes proximal and distal end portions with an intermediate, normally flexible main body portion. The main body portion includes an array of segments that, although individually pivotable with respect to each other, can be rendered into a rigid unit by engagement with interfering members. The interfering members prevent flexion of the prosthesis to enable the prosthesis to support the penis in a erectile condition. The prosthesis is manually manipulable to establish the penis in an erectile condition or a flaccid condition as desired.

20 Claims, 3 Drawing Sheets

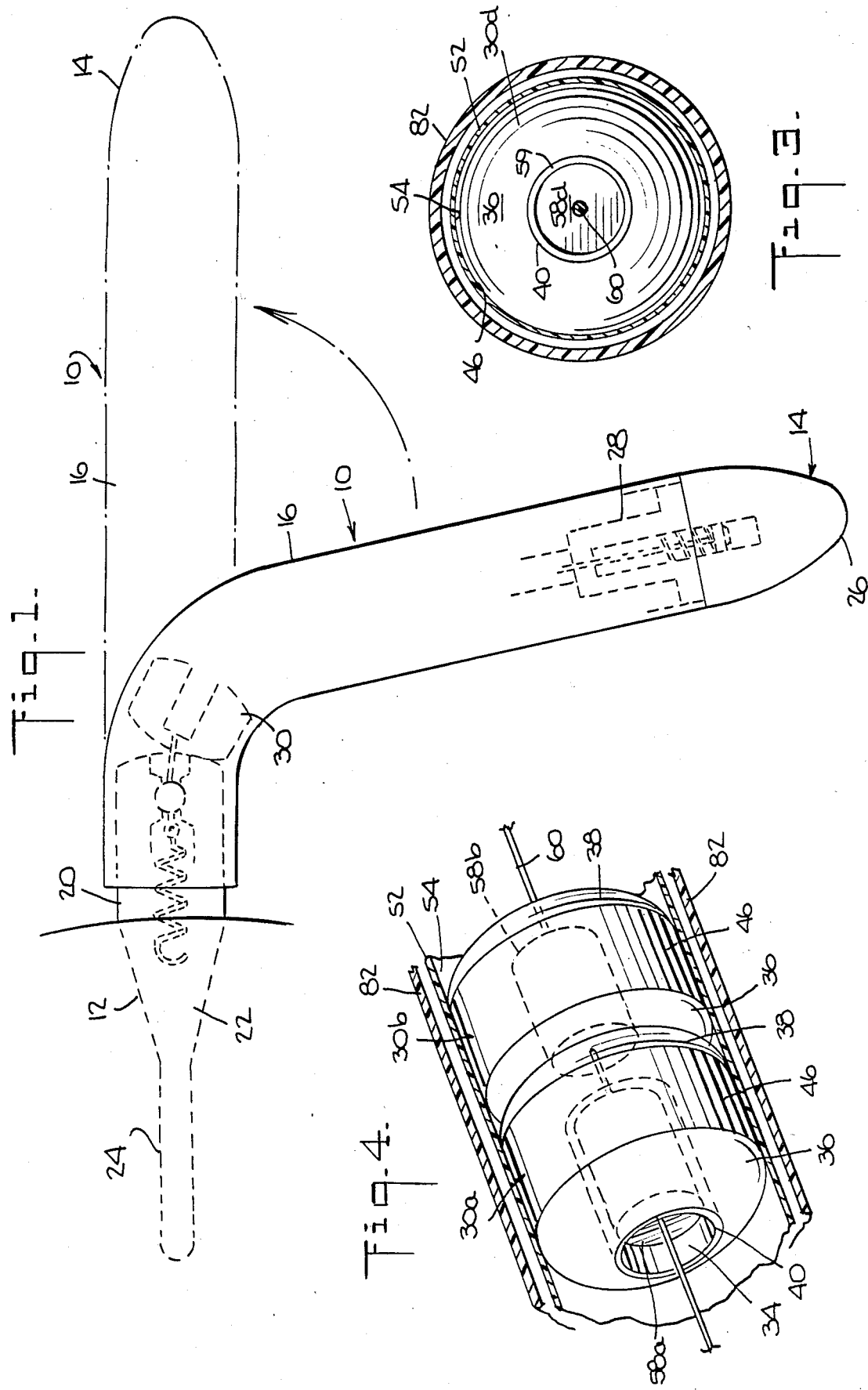

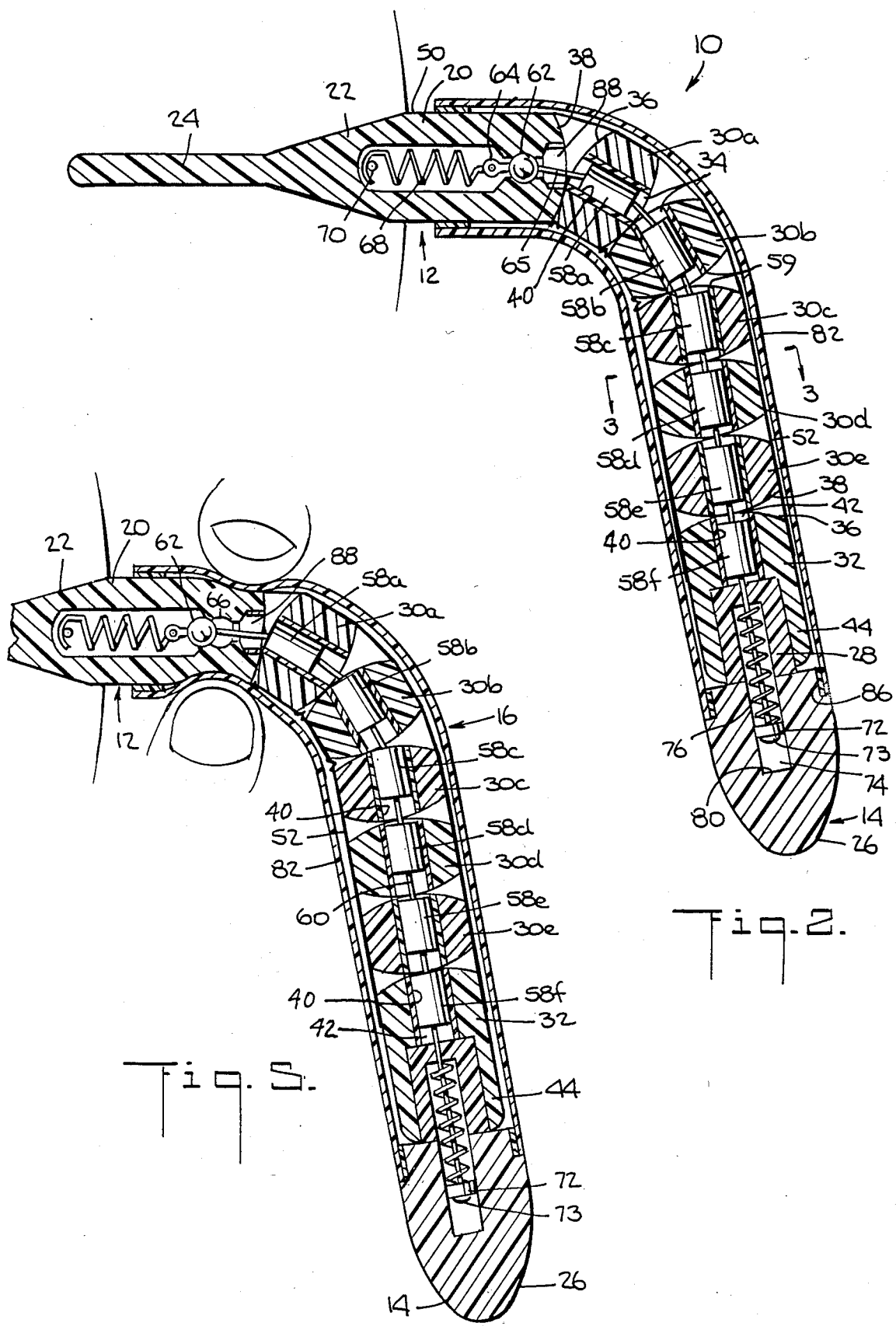

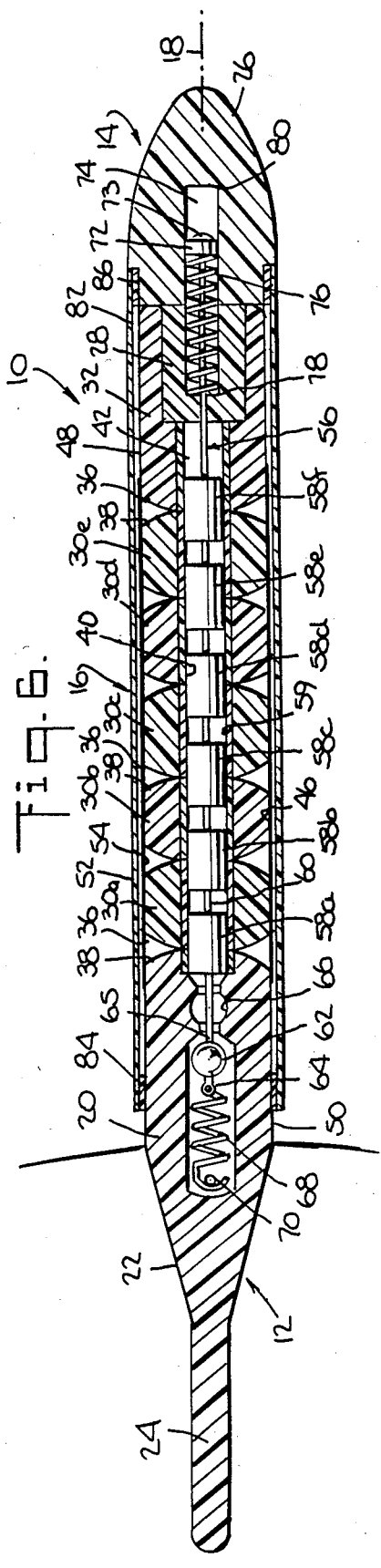
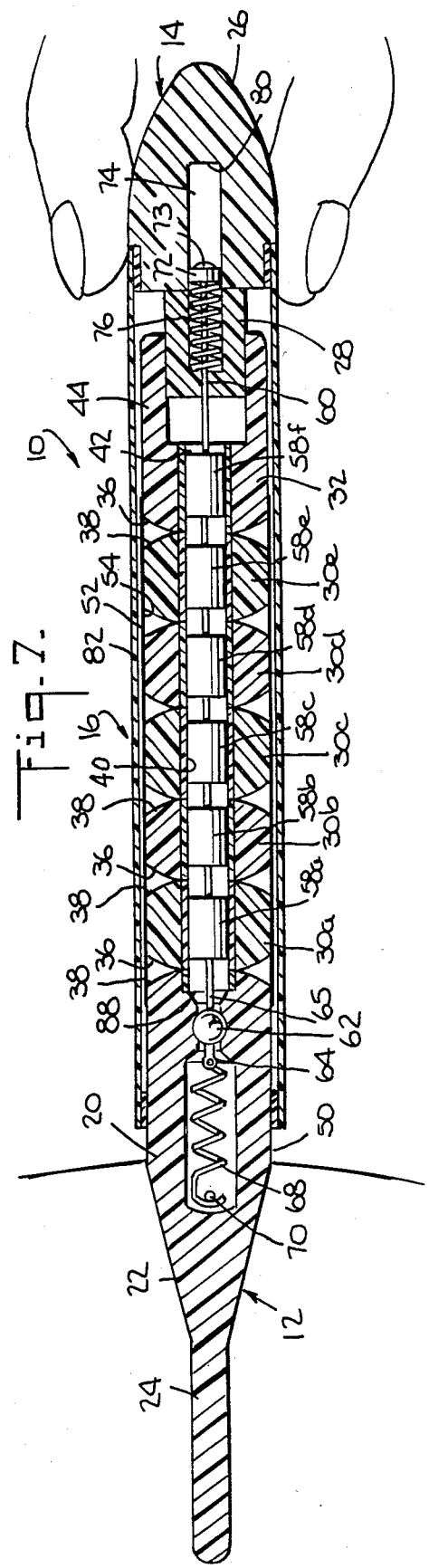

PENILE PROSTHESIS AND METHOD

BACKGROUND OF THE INVENTION

This invention relates to a penile prosthesis and method for selectively establishing an erectile condition in a penis and permitting the penis to return to a flaccid condition.

Prosthetic devices for supporting the penis in an erectile condition have long been used to compensate for erectile dysfunctions that otherwise prevent an individual from having an erection. Although many penile prostheses provide the penis with adequate erectile support, they do not allow the penis to return to a flexible, flaccid condition.

Some known prosthetic devices which support the penis in an erectile condition also permit the penis to assume the posture of a flaccid condition. For example, U.S. Pat. Nos. 3,893,456 and 4,151,840 show prosthetic penile devices which can also be bent to a selected curvature that corresponds to the posture of a flaccid penis. However, the flexural stiffness of these prosthetic devices prevent the penis from having the free flexibility that is normally associated with a flaccid penis, and can thus be discomforting.

Ideally, a prosthetic penile device should enable an individual to have an erectile condition when desired and should also permit restoration of the penis to a flexible, flaccid condition when desired.

Other known penile prostheses, such as shown in U.S. Pat. Nos. 4,522,198, 4,517,967 and 4,541,420 attempt to deal with the problem of restoring a prosthetically supported penis to a flaccid condition. The disclosed prosthetic devices have a relatively flexible mode and a relatively erectile mode. However these prosthetic devices rely on a high tension element having a complex actuation system to maintain the penis in an erectile condition. Relaxation of the tensioning element places the prosthetic device in the relatively flexible mode. However, If the tensioning element elongates as a result of tensioning stresses imposed thereon, it must be readjusted or it will lose the ability to support the penis in an erectile condition.

It is thus desirable to provide a penile prosthesis, of relatively simple construction, which is easily controlled to support the penis in an erectile condition, without the need for a high tension support element, and is easily adjusted to permit restoration of the penis to a substantially flaccid condition.

OBJECTS AND SUMMARY OF THE INVENTION

Among the several objects of the invention may be noted the provision of a novel penile prosthesis, a novel penile prosthesis which has a relatively flexible main body portion that can be rigidified as desired, a novel penile prosthesis having an array of segments that can be pivoted relative to each other to conform to the contour of a flaccid penis, a novel penile prosthesis which can be manually manipulated to place the penis in an erectile condition, a novel penile prosthesis which can be manually manipulated to restore the penis to a flaccid condition from an erectile condition, and a novel method for selectively establishing a flaccid or erectile condition in a penile prosthesis.

Other objects and features of the invention will be in part apparent and in part pointed out hereinafter.

The penile prosthesis, in accordance with one embodiment of the invention, includes proximal and distal end portions with a flexible main body portion provided intermediate the proximal and distal end portions. The main body portion includes a plurality of segments arranged side by side to permit relative pivotal movement or articulation with respect to each other such that the main body portion, as a unit, is freely flexible. The free flexibility of the main body portion enables the penis to maintain a substantially flaccid condition.

A nonextensible flexible sheath encases part of the proximal end portion and the segments which are also peripherally adhered to the sheath. An extensible flexible sheath, joined to the proximal and distal end portions, surrounds the nonextensible sheath. Under this arrangement, the distal end portion is longitudinally movable with respect to the segments.

The prosthesis also includes stiffening means that are longitudinally movable relative to the main body portion, from a first position that does not affect the flexibility of the main body portion, to a second position that maintains the main body portion in a substantially straight rigidified configuration to support a penis in a substantially erectile position. Thus, the stiffening means, when disposed in the first position enable the penis to assume a posture that corresponds to the posture of a flaccid penis due to the free flexibility of the main body portion.

When the stiffening means are moved from the first position to the second position they engage the segments of the main body portion in a manner that restrains the main body portion from bending, by preventing the segments from pivoting or articulating with respect to each other. The stiffening means are thus positioned to rigidify the main body portion, thereby preventing the prosthesis from bending as a unit.

The stiffening means are joined to the proximal and distal end portions of the prosthesis. However the distal end portion is longitudinally movable with respect to the segments. Movement of the distal end portion away from the segments causes movement of the stiffening means from the second position wherein the prosthesis is substantially unflexible and unbendable, to the first position wherein the main body portion of the prosthesis is flexible.

Detent means provided in the proximal end portion, for example, and on the stiffening means, detent the stiffening means in the first and second positions.

The proximal end portion is manually deformable to overcome the detent in the first position and enable the stiffening means to move to the second position. Biasing means which move the stiffening means from the first position to the second position also serve to detent the stiffening means in the second position.

The prosthesis can thus be manipulated while in its implanted position in the penis to accomplish movement of the stiffening means from the first position to the second position and vice versa.

The invention accordingly comprises the constructions and method hereinafter described, the scope of the invention being indicated in the claims.

DESCRIPTION OF THE DRAWINGS

In the accompanying drawings,

FIG. 1 is a simplified schematic view of a penile prosthesis incorporating one embodiment of the invention and showing movement of the penile prosthesis from a position permitting penile flaccidity (hereinafter referred to as flaccid condition) to a position that establishes an erectile condition of the penis (hereinafter referred to as erectile condition);

FIG. 2 is a sectional view thereof in the flaccid condition;

FIG. 3 is a sectional view taken on the line 3—3 of FIG. 2;

FIG. 4 is a fragmentary perspective view thereof, partially shown in section;

FIG. 5 is a simplified cutaway view, with section lines omitted for the purposes of clarity, showing the prosthesis in the flaccid condition being actuated for movement to the erectile condition;

FIG. 6 is a sectional view thereof showing the prosthesis in the erectile condition; and FIG. 7 is a simplified cutaway view, with section lines omitted for the purposes of clarity, showing the prosthesis in the erectile condition being actuated for movement to the flaccid condition.

Corresponding reference characters indicate corresponding parts throughout the several views of the drawings.

DETAILED DESCRIPTION OF THE INVENTION

A penile prosthesis incorporating one embodiment of the invention is generally indicated by the reference number 10 in FIG. 1.

The prosthesis 10 comprises a proximal end portion 12, a distal end portion 14 and a main body portion 16 extending from the proximal end portion 12 to the distal end portion 14.

The prosthesis 10 has a predetermined longitudinal extent along a longitudinal axis 18, as shown in FIG. 6. Further references to the term longitudinal are intended to refer to magnitudes or directions relative to the longitudinal axis 18.

The proximal end portion 12, which is formed of a relatively firm medical grade elastomer, includes a generally cylindrical section 20, a tapered conical section 22, and a rod-like mounting section 24 that extends from the tapered section 22.

The distal end portion 14 is preferably formed of two pieces, one of which is a conically tapered, gently curved free-end 26 formed from a soft medical grade elastomer, the other piece being an opposite reduced end 28, formed of a relatively firm medical grade elastomer.

The main body portion 16 includes a plurality of annular members or segments 30a, 30b, 30c, 30d and 30e that are positioned side-by-side from the proximal end portion 12 and a terminal segment 32 disposed adjacent the distal end portion 14. Thus the adjacently disposed segments 30a–30e and 32 have an overall longitudinal extent that spans the proximal and distal end portions 12 and 14. Preferably the segments 30a–30e and 32 are formed of a firm medical grade elastomer and equipped with stainless steel sleeves 40.

As most clearly shown in FIG. 4, a typical segment 30a has a central axial opening 34 and opposite end portions 36 and 38 of convex curvature that intersect the opening 34. The sleeve 40 borders the opening 34.

The terminal segment 32 has a central axial opening 42 in alignment with and of identical diameter with the opening 34. The sleeve 40 borders the opening 42. The terminal segment 32 also has a curved end portion 36, and further includes an annular wall portion 44 that surrounds, but does no bind the reduced portion 28 of the distal end 14.

The segments 30a–30e each have a peripheral surface 46. The terminal segment 32 and the proximal end portion 12 have respective peripheral surfaces 48 and 50 of corresponding diameter with the peripheral surface 46 of the segments 30a–30e.

A nondistensible sheath 52 is bonded to the cylindrical section 20 of the proximal end portion 12 near the convex portion 38. The peripheral surfaces 46 of the segments 30a–30e and part of the peripheral surface 48 of the terminal segment 32 are bonded to an inner surface 54 of the sheath 52. Preferably the sheath 52 is formed of a biocompatible fabric such as woven teflon.

The prosthesis 10 further includes stiffening means 56 that prevent the main body portion 16 from bending, by maintaining the main body portion 16 in a rigidified, substantially straight configuration to support a penis (not shown) in a substantially erectile position.

The stiffening means 56 comprise a plurality of generally cylindrical rigid interference members 58a, 58b, 58c, 58d, 58e, and 58f, which can be formed of polysulfone, slidably disposed within the central openings 34 and 42 of the segments 30a–30e and 32. The longitudinal extent of the interference members 58a–58e is less than the longitudinal extent of the segments 30a–30e and 32. Thus, the interference members 58a–58f can be entirely recessed in the openings 34 and 42 of the segments 30a–30e and 32. A lubricant 59, such as a silicone gel, lines the inner surfaces of the central openings 34 and 42.

The stiffening means 56 include a flexible non-extensible connecting member 60 such as a cable or cord that joins the interference members 58a–58f in a predetermined spaced relationship. The opposite ends of the connecting member 60, which can be formed of braided stainless steel wire or high tensile polymer cord such as nylon or dacron, extend into the proximal and distal end portions 12 and 14.

A detent ball 62, with an extended eye piece 64, is joined to a proximal end 65 of the connecting member 60. The detent ball 62 is normally seated in a socket 66 formed in the proximal end portion 12. The eye piece 64 engages a proximal biasing spring 68 anchored against a post 70 in the proximal end portion 12.

A slide piece 72 is joined to a distal end 73 of the connecting member 60 for slideable movement in an elongated passage 74 formed in the distal end portion 14. Access to the passage 74 can be obtained by forming the distal end portion 14 in two pieces. A distal cushioning spring 76 is disposed between the slide piece 72 and an end 78 of the passage 74. The distal cushioning spring 76 has a longitudinal magnitude less than the extent of the passage 74 from the end 78 to an opposite end 80.

A flexible, extensible outer sheath 82 extends from the proximal end portion 12 to the distal end portion 14. The sheath 82 is joined at 84 to the proximal end portion 12, and is joined at 86 to the distal end portion 14. The movable inner workings of the penile prosthesis 10 are thus enveloped within the outer sheath 82 and the inner sheath 52.

The prosthesis 10 is implanted in the penis (not shown) in any suitable known manner and can be manually manipulated from the normally flaccid condition, of FIG. 1, to the erectile condition also shown in dotted outline in FIG. 1.

Referring to FIG. 2, when the prosthesis is in its normally flaccid condition, the interference members 58a–58f are entirely recessed in the segments 30a–30e and 32 and do not interfere with the bending of the main body portion 16 of the prosthesis 10. The engagement of the detent ball 62 in the socket 66 at the proximal end portion 12 and the biasing force of the distal spring 76 maintain the recessed position of the interference members 58a–58f.

Since the interference members 58a–58f are entirely recessed within their respective segments, the segments 30a–30e and the terminal segment 32 are free to bend, pivot or articulate with respect to each other about the curved end portions 36 and 38. The prosthesis 10 is thus enabled to conform to the flaccid contour of the penis.

It should be noted that the penile prosthesis 10, when placed in the flaccid condition, does not support the penis but follows the flaccid contour of the penis due to the free flexibility of the main body portion 16. The prosthetically supported penis can thus achieve flexibility in a manner closely akin to that of a normally flaccid penis.

The prosthesis 10 is placed in the erectile position of FIGS. 1 and 6 by gently deforming the proximal end portion 12 in the area of the ball and socket detent arrangement 62,66 in the manner shown in FIG. 5. The socket 66 has a smaller opening at the right extremity, as viewed in FIG. 5, than at the left extremity. Thus when the proximal end portion 12 is deformed as shown, the ball 62 tends to unseat from the socket 66 and move toward the left, under the influence of the proximal biasing spring 68.

Movement of the ball 62 by the proximal biasing spring 68 causes the connecting member 60 to shift the interference members 58a–58f toward the proximal end 12 until the interfering members 58a–58f bridge the convex ends 36 and 38 of two adjacent segments such as shown in FIG. 6.

A recess 88 (FIGS. 2 and 5), receives the interfering member 58a. The interfering member 58a thus bridges the proximal end 12 and the segment 30a, preventing the segment 30a from bending with respect to the proximal end 12. The interference member 58b bridges the segments 30a and 30b preventing the segment 30b from bending with respect to the segment 30a and vice versa. In similar fashion the additional interference members 58c–58e bridge the adjacent segments 30c–30e preventing the segments 30c–30e from bending with respect to each other. The interference member 58f bridges the segments 30e and 32 preventing any bending therebetween. The segments 58a–58f, when placed in the second position, as shown in FIG. 6, render the prosthesis non-bendable to support the penis in an erectile condition.

The erectile condition of FIG. 6 is maintained as long as the interfering members 58a–58f bridge the respective adjacent segments 30a–30e and 32. Since the interfering members 58a–58f extend well beyond the contact point at the rim portions 40 between adjacent segments, and the proximal end portion 12, slight movements of the interfering members 58a–58f within the segments 30a–30e and 32 will not upset the erectile condition. The interfering members 58a–58f are maintained in their FIG. 6 positions without subjecting the connecting member 60 to any substantial tension stresses. The proximal biasing spring 68 is merely a device for moving and maintaining the interfering members 58a–58f to the desired position and not for maintaining the connecting member 60 under high tension.

The prosthesis 10 will maintain its erectile condition until the ball 62 is reseated in the socket 66. The reseating process is accomplished in the manner shown in FIG. 7 by grasping the distal end portion 14 of the prosthesis 10 and gently extending it away from the proximal end portion 12. Such movement of the distal end portion 14 causes the distal biasing spring 76 to compress in a smooth, gentle manner and place a gradual tension on the connecting member 60 to overcome the force of the proximal biasing spring 68 and draw the ball 62 back into the socket 66. Since the proximal end portion 12 is deformable, the ball 62 can be reseated in the socket 66, as shown in FIG. 7. A flaccid condition of the penis can then be restored.

Thus, gentle manipulation of the penile prosthesis will enable the user to establish a erectile penile condition or a flaccid penile condition as desired.

Some advantages of the present invention evident from the foregoing description includes a prosthesis having sufficiently flexible characteristics for restoring the penis to a substantially flaccid condition when desired, and manually actuatable stiffening means for supporting the prosthesis in an erectile condition. A further advantage is that either the erectile condition or the flaccid condition can be easily provided by a simple manipulation by the prosthesis through the penis. A further advantage is that the prosthesis, when placed in the flaccid condition, has sufficient flexibility to conform to the flaccid contour of the penis, thereby affording the user the comfort enhancements of a flaccid penile condition.

In view of the above, it will be seen that the several objects of the invention are achieved and other advantageous results attained.

As various changes can be made in the above constructions and method without departing from the scope of the invention, it is intended that all matter contained in the above description or shown in the accompanying drawings shall be interpreted as illustrative and not in a limiting sense.

What is claimed is:

1. A penile prosthesis comprising,
(a) a proximal end portion and a distal end portion,
(b) a flexible main body portion intermediate said proximal and distal end portions, said main body portion having a predetermined plurality of segments arranged side-by-side to permit relative movement with respect to each other in a predetermined direction,
(c) stiffening means engageable with said main body portion, for rendering said main body portion substantially inflexible, said segments each having at least a first predetermined longitudinal magnitude along a longitudinal axis of said prosthesis, said stiffening means including a predetermined plurality of interference members having not greater than a second predetermined longitudinal magnitude along said longitudinal axis, said second predetermined longitudinal magnitude being less than said first predetermined longitudinal magnitude,
(d) said stiffening means being disposable in a first position relative to said main body portion to permit said main body portion to remain flexible such that said main body portion can bend and assume a contour that corresponds to the contour of a flaccid penis,
(e) said stiffening means being disposable in a second position of predetermined engagement with said main body portion to prevent said main body portion from bending and to maintain said main body portion in a substantially straight configuration, to support a penis in a substantially erectile position.

2. The prosthesis as claimed in claim 1 wherein said segments are separate and unjoined.

3. The prosthesis as claimed in claim 1 wherein said segments each have opposite end portions that are intersectable with the longitudinal axis and said interference members are positioned intermediate the opposite end portions of said segments when said stiffening means is in said first position.

4. The prosthesis as claimed in claim 3 wherein said segments are in abutting contact with each other at said opposite end portions when said stiffening means is in said second engaged position and said interference members are positioned to respectively bridge the abutting opposite end portions of respective adjacent segments when said stiffening means is in said second position.

5. The prosthesis as claimed in claim 4 wherein said segments are of annular shape with respective central openings and said interference members are receivable in the respective openings of said segments.

6. The prosthesis as claimed in claim 4 including connecting means for connecting said interference members together for uniform movement of said stiffening means from said first position to said second position and vice versa.

7. The prosthesis as claimed in claim 1 including means for holding said stiffening means in either of said first and second positions.

8. The prosthesis as claimed in claim 7 wherein said holding means comprise detent means provided on said stiffening means and at least one of said proximal and distal end portions.

9. The prosthesis as claimed in claim 8 wherein said detent means comprise a ball and socket joint on said stiffening means and said proximal end portion, to detent said stiffening means in one of said first and second positions.

10. The prosthesis as claimed in claim 9 wherein said ball and socket joint is deformable to release said detent.

11. The prosthesis as claimed in claim 10 wherein said detent means comprise biasing means provided on one of said proximal and distal end portions and joined to said stiffening means to detent said stiffening means in one of said first and second positions.

12. The prosthesis as claimed in claim 11 wherein said biasing means is elongatable to overcome said detent.

13. The prosthesis as claimed in claim 12 including actuating means for causing movement of said stiffening means to elongate said biasing means and enable said stiffening means to move from one of said positions to the other said position.

14. The prosthesis as claimed in claim 13 wherein said biasing means is provided in the proximal end portion and said actuating means comprise said distal end portion being connected to said stiffening means and being movable with respect to said main body portion for movement of said stiffening means from said first position to said second position.

15. The prosthesis as claimed in claim 14 wherein the connection between said stiffening means and said distal end portion is resilient.

16. The prothesis as claimed in claim 1 including a terminal segment at the distal end portion and wherein a flexible, substantially nonextensible first sheath joins said proximal end portion and said terminal segment, the other said segments being confined within said first sheath and being adhered to said first sheath.

17. The prosthesis as claimed in claim 16 including an elongated flexible extensible outer sheath joining said proximal and distal end portions and surrounding said segments.

18. A method of selectively establishing a flaccid or erectile condition in a penile prosthesis comprising,
   (a) providing individual segments intermediate a proximal and distal end of the prosthesis, the segments being arranged side by side to articulate and bend as a unit to enable the prosthesis to assume a contour that corresponds to the flaccid condition of a penis,
   (b) interfering with the bending freedom of the segments by engaging each pair of adjacent segments and one of the proximal and distal end portions with a rigid member that prevents bending of the segments and locks the array of segments in an unbent, substantially straight configuration to support a penis in a substantially erectile position,
   (c) detenting the rigid members in the interfering position when the erectile condition is desired,
   (d) moving the rigid members uniformly from the interfering position to a non-interfering position when a flaccid penile condition is desired, and
   (e) detenting the rigid members in the non-interfering position when the flaccid penile condition is desired.

19. The method of claim 18 including rendering the prosthesis manually elongatable to overcome the detent of the rigid members in the erectile condition and accomplish movement of the rigid members from the interfering position to the non-interfering position.

20. The method of claim 18 including rendering the prosthesis manually deformable to overcome the detent of the rigid members in the flaccid condition and accomplish movement of the rigid members from the non-interfering position to the interfering position.

* * * * *